(12) United States Patent
Failes

(10) Patent No.: US 7,136,167 B2
(45) Date of Patent: Nov. 14, 2006

(54) FIBER OPTIC SCANNING INTERFEROMETER USING A POLARIZATION SPLITTING COUPLER

(76) Inventor: Michael Failes, 1155 Appleby Line, Unit E8, Burlington, Ontario (CA) L7L 5H9

( * ) Notice: Subject to any disclaimer, the term of this patent is extended or adjusted under 35 U.S.C. 154(b) by 224 days.

(21) Appl. No.: 10/796,320

(22) Filed: Mar. 10, 2004

(65) Prior Publication Data

US 2005/0099633 A1 May 12, 2005

(30) Foreign Application Priority Data

Nov. 6, 2003 (CA) .................................. 2448346

(51) Int. Cl.
*G01B 9/02* (2006.01)
(52) U.S. Cl. ....................................... 356/479
(58) Field of Classification Search ................ 356/477, 356/479, 491; 250/227.19, 227.27
See application file for complete search history.

(56) References Cited

U.S. PATENT DOCUMENTS

| | | | |
|---|---|---|---|
| 4,861,127 A * | 8/1989 | Failes ........................... 385/42 |
| 5,459,570 A * | 10/1995 | Swanson et al. ............ 356/479 |
| 5,835,642 A | 11/1998 | Gelikonov et al. |
| 5,867,268 A | 2/1999 | Gelikonov et al. |
| 6,441,356 B1 * | 8/2002 | Mandella et al. ........ 250/201.3 |
| 6,522,407 B1 | 2/2003 | Everett et al. |
| 6,608,684 B1 | 8/2003 | Gelikonov et al. |

* cited by examiner

*Primary Examiner*—Gregory J. Toatley, Jr.
*Assistant Examiner*—Michael A. Lyons
(74) *Attorney, Agent, or Firm*—Riches, McKenzie & Herbert LLP

(57) ABSTRACT

A fiber optic scanning interferometer in a Michelson arrangement using a polarization splitting coupler is disclosed. The splitting of s and p polarization modes into the fast and slow axes of a birefringent fiber allows the temporal separation of interference phenomena from multiple reflections such that signal recovery is simplified.

12 Claims, 5 Drawing Sheets

Figure 1a
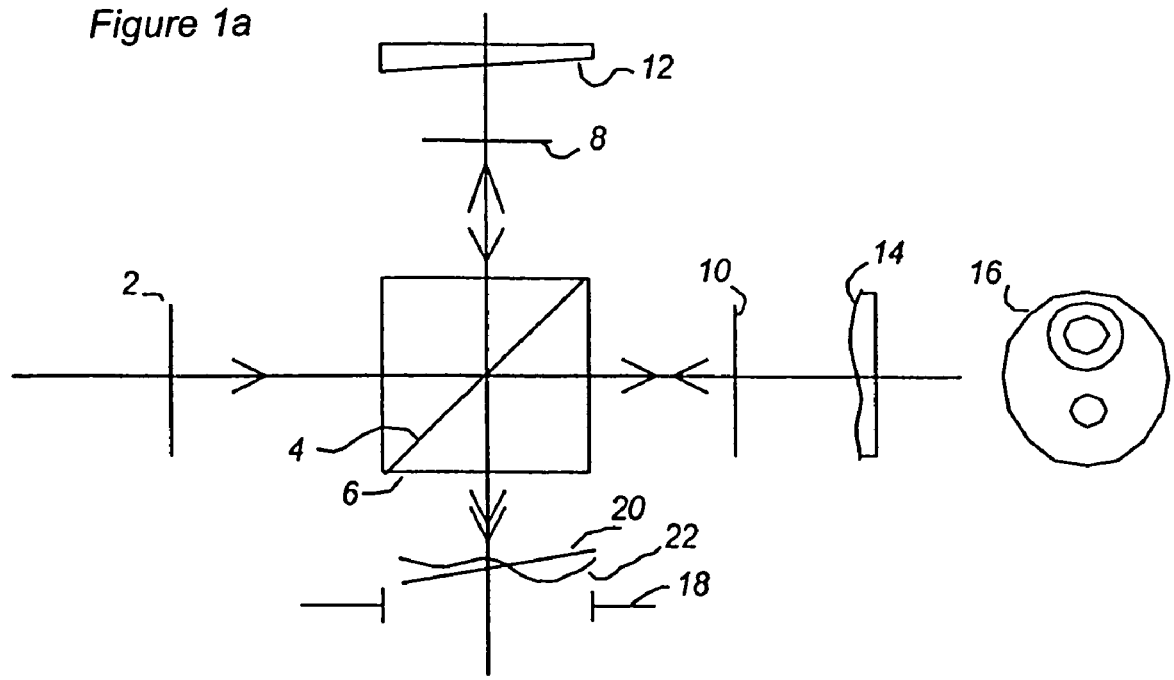
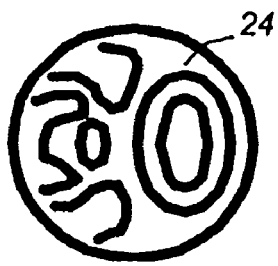
Figure 1b
PRIOR ART

FIBER OPTIC SCANNING INTERFEROMETER USING A POLARIZATION SPLITTING COUPLER

BACKGROUND OF THE INVENTION

1. Field of the Invention

In the application to optical coherence tomography, there is a need to detect reflecting and scattering targets within a sensing volume to determine the spatial distribution of the targets. The use of low coherence laser sources allows detection of reflecting and scattering targets by scanning optical paths through the zero path difference condition under which fringes can be observed. In the application to polarization mode dispersion (PMD), the source has passed through a long singlemode fiber and has accumulated phase and amplitude changes due to birefringence effects in that fiber which manifest as polarized modes which can be analyzed by observation of the fringes generated in a scan.

2. Discussion of the Prior Art

There are many descriptions of fiber optic interferometers with optical path length modulation that give fringes. These devices are made in single mode (SM) standard fibers that exhibit random changes in polarization state due to environmental conditions and can be compensated to some extent by the use of polarization controllers. Interferometers made in polarization maintaining (PM) fiber are usually restricted to one axis of polarization and have polarization stability, although cross coupled components give rise to unwanted modulation effects. Where a PM fiber has both axes transmitting light, the interference in each axis will generally be different and must be separated to give a useful device.

SUMMARY OF THE INVENTION

The present invention relates generally to the separation of the polarization modes into slow and fast axes of a birefringent fiber.

In general, a broad band source used with an interferometer has the effect of producing a burst of fringes centered about the zero optical path difference condition. A scanning interferometer can therefore give information about the source or the reflecting elements in the optical path by observation of the fringe pattern. The application to optical coherence tomography will be described to illustrate one aspect of the invention.

The application of a fiber optic interferometer to optical coherence tomography uses the property of a broad band source, where optical path length scanning results in a burst of fringes within a narrow envelope that is dependent on the distribution and reflectivity of reflecting or scattering elements of the target. If a simple distance measurement for discrete reflectors is required, then the shape and intensity of envelopes that compose the signal is not particularly important. When the target is complex in reflectivity and distribution of reflecting elements, then the multiple and complex envelopes require some analysis to relate them to the target.

Polarization maintaining (PM) fiber that is manufactured with built in birefringence can be shown to maintain a plane polarized mode that is launched into one of the polarization maintaining axes. This is a most effective way to eliminate polarization mode dispersion and polarization rotation within the fiber itself. When interferometers are made with polarization preserving fiber, the effect of cross coupling from components and splices in the fiber path can produce unwanted signals due to the multiple optical paths that can occur as the cross coupled components propagate down both fast and slow axes of the fiber. In cases where several polarization sensitive components are cascaded along a fiber path, the problem is intensified.

If laser light that is not plane polarized is used to illuminate a polarization maintaining fiber, some means must be found to separate the p and s polarization modes propagating in the fast and slow axes. As the axes have a relatively large difference in the propagation constant, the PM fiber acts as if it were two coincident interferometers on the fast and slow axes of the fiber. These interferometers do not give phase matched fringes at the zero optical path difference condition due to minor variations in the propagation constants. If the source has a bandwidth such that the burst of fringes at the zero optical path condition is several hundred fringes wide, then the difference in the propagation constants will cause beating of the p and s mode fringes. Cross coupling in components and splices of the interferometer will also contribute to unwanted signals at the zero path difference condition.

Standard (non polarization maintaining) singlemode fiber (SM) has residual birefringence from the manufacturing process as well as that caused by interferometer layout where bends and thermal stress cause small birefringence effects. It is usually very small compared to PM fiber birefringence. This birefringence produces polarization mode dispersion that has only a small phase difference between modes compared to the many phase oscillations that occur during the burst of interference fringes at near zero optical path difference. The dispersed components that are output from a SM fiber are usually referred to as the principal states of polarization and are not generally aligned with any other axes. There is also polarization rotation due to fiber bends. In a SM fiber optic interferometer some means of selecting polarization modes that are in the same state is needed such that interference can be obtained. This means is generally complex and difficult to implement.

A Michelson interferometer that uses a polarizing beam splitter coupler, where the signal is in the p mode and the reference signal is in the s mode, has the advantage that the zero optical path difference condition is not coincident with the zero physical path difference of the fiber arms. The p-signal and s-reference modes can be beat together by placing an analyzer at 45 degrees to the fiber axes. The orthogonal p-reference and s-signal modes have a large optical path difference in this condition and are therefore temporally separated and appear at a different time on a fringe scan.

BRIEF DESCRIPTION OF THE DRAWINGS

FIG. 1a is a general representation of a Michelson interferometer showing an output fringe pattern from an irregular reflector;

FIG. 1b illustrates the interference pattern of light and dark bands produced by the Michelson interferometer of FIG. 1a.

PREFERRED EMBODIMENT OF THE INVENTION

Figure 2:
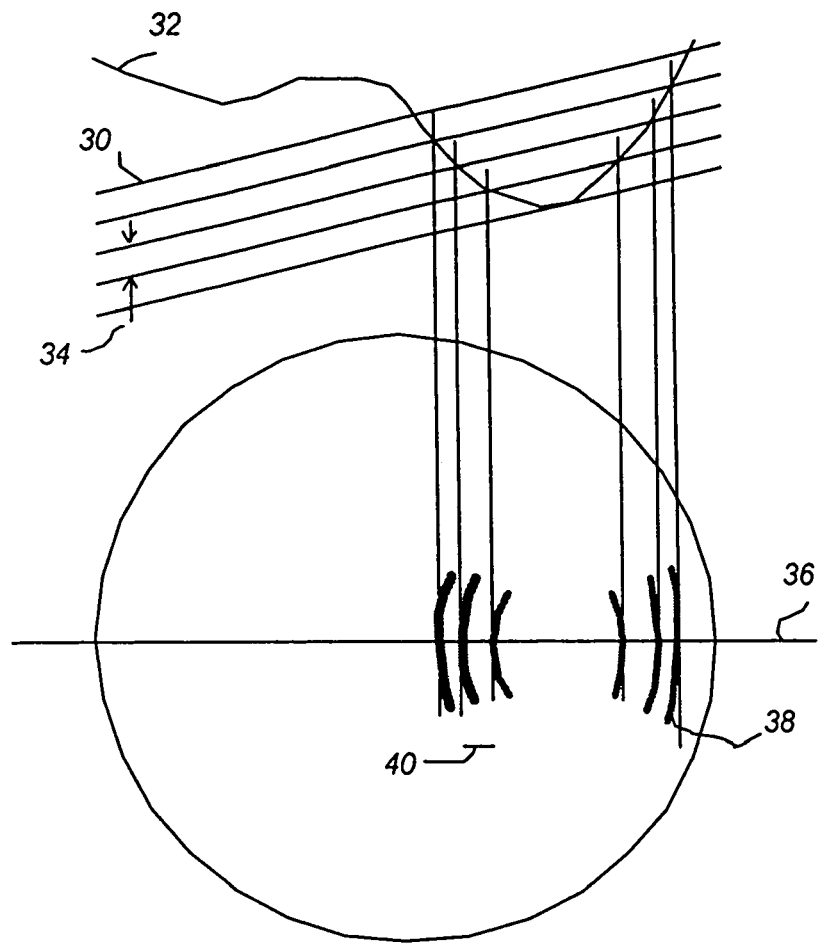
FIG. 2 shows the details of the fringe pattern in FIG. 1.

The following illustrates the essential attributes of interferometry for understanding of the invention.

A Michelson interferometer is shown in FIG. 1. This arrangement demonstrates the phenomenon of optical interference between two wave fronts.

A source plane wavefront 2 is split by the diagonal face 4 of the beam splitter cube 6 into the plane wavefront 8 by reflection and plane wavefront 10 by transmission. Mirror 12, shown with a small tilt reflects the plane wavefront 8 which is transmitted by the beam splitter cube 6 to the output aperture 18 where it appears as a tilted wavefront 20. Mirror 14, shown with surface irregularity 16, reflects the plane wavefront 10 which is in turn reflected by the beam splitter cube 6 to the output aperture 18 where it appears as an irregular wavefront 22. The superposition of the wavefronts 20 and 22 gives the interface pattern of light and dark bands 24 (see FIG. 1b) called fringes.

The observed intensity of the fringes is the square of the amplitude of the resultant superposition. It is well understood from theory that superposition of transverse waves of the form $Y=A \sin 2\pi(\omega t-\alpha)$ and $Z=B \sin 2\pi(\omega t-\beta)$ with respect to phase $\alpha$ and $\beta$ and amplitudes A and B gives $R=C \sin 2\pi(\omega t-\chi)$ where $\chi$ is the new phase and the intensity is $C^2$. Amplitudes A and B are determined by the reflectivity of the beam splitter cube, mirrors and any attenuating optics within the optical path.

FIG. 2 shows the fringes with respect to the phase of the superposed wavefronts. The phase difference ($\alpha-\beta$) between the wavefronts 30 and 32 is shown as a propagation distance 34 and an observed fringe spacing 40 in the pattern 38, partially illustrated along a diameter 36. As phase is equal to $2\pi z/\lambda$ where z is the distance along the axis of propagation and $\lambda$ the wavelength. At every repeated interval of $2\pi$ where $z=N\lambda$ and N is an integer, the light and dark bands repeat.

Wavefronts also combine and return in the direction of the source with a $\pi$ phase difference.

Referring to FIG. 1, if the mirror 12 is set normal to the optical axis and mirror 14 is made plane and normal to the optical axis, the result is a single fringe across the whole aperture 18, the intensity of which is determined by the phase difference between these superposed, plane and parallel wavefronts. If mirror 14 moves at a constant rate v along the axis, the phase changes at the frequency of $2v/\lambda$ and the fringe appears to modulate bright and dark. The above representation is known as a "bulk optic" interferometer to distinguish it from a "fiber optic" interferometer.

As stated before, the essence of the invention relates to the separation of the polarization modes into the fast and slow axes of a birefringent fiber. In one embodiment, this is accomplished by using a polarization splitting fiber optic coupler, that is, a coupler that has both fast and slow axes light input and separates the modes into S on the reference arm and P in the signal arm. This is the analog of a polarizing cube beam splitter.

This allows the cross coupled components, these being the small amount of P mode light that is spilled into the S mode, and vice versa, to be temporally separated in an optical path length modulating or scanning interferometer. That is the burst of fringes will be observed at different times, which is a different phase, within a sinusoidal or triangle wave scan. It also allows for inefficient polarization splitting where the P and S are not fully separated as this appears similar to cross coupling.

Cross coupled components are therefore eliminated from the burst of fringes that are the desired signal.

Figure 3:
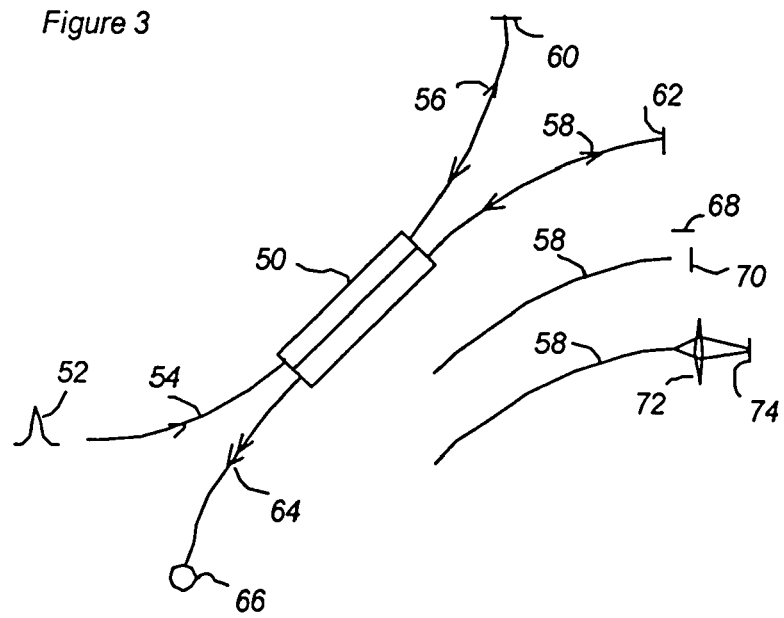
FIG. 3 shows a fiber optic coupler (beam splitter/combiner) arranged as a Michelson interferometer with alternative air paths at the fiber terminations.

In the singlemode fiber optic interferometer shown in FIG. 3, a fiber optic coupler 50 replaces the cube beam splitter of FIG. 1, as a similar four port device. The end terminations can have auxiliary optics to complete the retro-reflection of the beams.

A single mode propagated in a single mode fiber is equivalent to a plane wavefront perpendicular to the optical axis in a bulk optic interferometer. One of the most useful attributes of fiber optic interferometers is this single mode property, where orientation and flatness of optical components is no longer a concern. One of the major problems of a fiber optic interferometer is changes in the state of polarization of the mode as it propagates along the fiber. Interference only occurs from the superposition of waves having the same state of polarization.

Referring to FIG. 3, the mode propagates through the fiber pigtail 54 to the coupler 50 where it is split into two modes propagating in the pigtails 56 and 58. The reflecting ends 60 and 62 reflect the modes back to the coupler where they are combined in both pigtails 54 and 64. The intensity at the detector 66 is a function of the amplitudes and phase difference of the combined (superimposed) modes just as in the bulk optic case. Changing the optical path of the fiber optic interferometer can be implemented by stretching the fiber to increase the optical path by physical or by thermal means. In this case it would be described as an intrinsic interferometer. In practical applications one path is called the reference path and the other the signal path.

If a small air gap 68 is made between the fiber pigtail 58 and a mirror 70, the air gap can be changed to give a phase variation. A lens 72 to image the tip of the fiber pigtail 58 onto a target 74 can also be used to increase the light collection of the pigtail 58 and extend the air path. These arrangements are known as combinations of intrinsic and extrinsic interferometers. An extrinsic interferometer is where the singlemode fiber is simply used to deliver light to an all bulk optic interferometer.

In the above explanation, the source is assumed to be a single wavelength, and the fringe modulation in response to phase change is constant and stretches to infinity, but in practice sources have a finite band width and fringe patterns are limited in range of phase.

Figure 4:
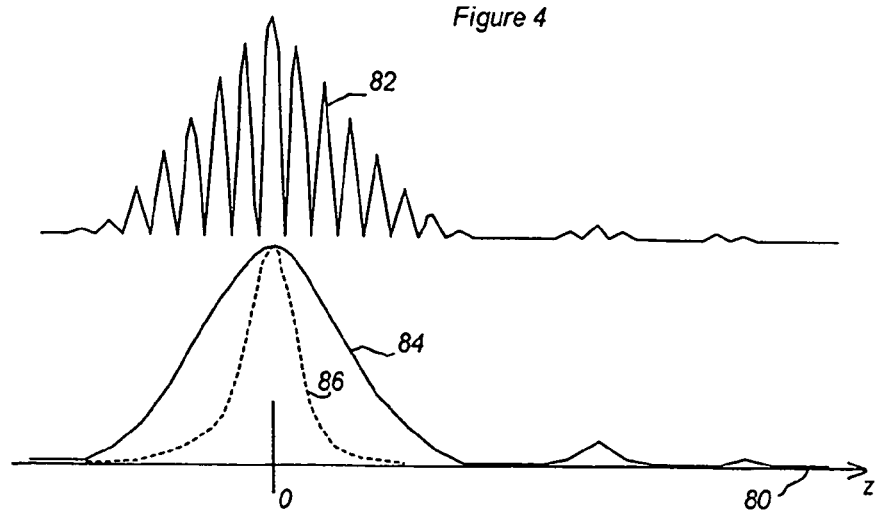
FIG. 4 shows the fringes that result from a finite source width.

Referring to FIG. 4, there are shown the fringes that result from a finite source width, the horizontal axis 80 representing the phase difference between interfering modes and the vertical axis representing the intensity of the fringes. It can be shown from theory that the fringe pattern 82 will have a maximum intensity at zero phase difference and the intensity will fall off as the phase difference increases either positively or negatively illustrated by the envelope curve 84. The envelope of the fringe pattern, illustrated as curve 84 will be a function of the source wavelength distribution and can be a very complicated function. Very broad band sources will give a narrow envelope 86.

Figure 5:
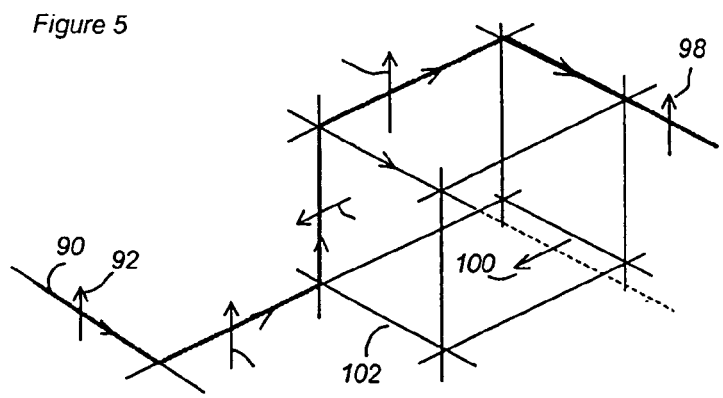
FIG. 5 illustrates polarization rotation.

Referring to FIG. 5, a rectangular grid 102 is used to show the alternate paths of a fiber 90 as it undergoes right angle bends and returns to its original direction at 98 and 100. The input mode is plane polarized vertically and can be seen to travel along the fiber with change in orientation as the fiber undergoes the bends. It can be seen that the alternate paths have resulted in polarization states 98 and 100 that are orthogonal.

Figure 6:
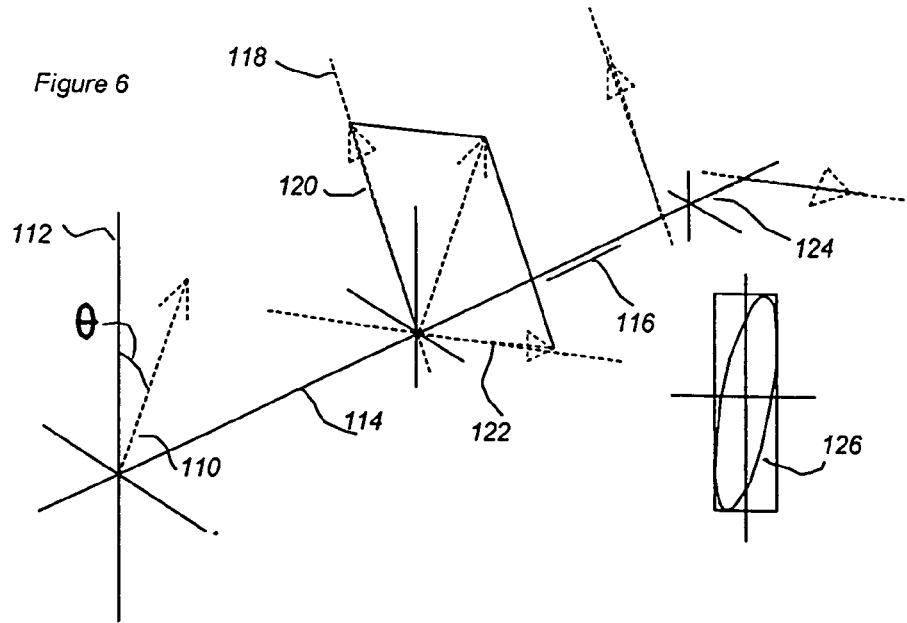
FIG. 6 illustrates polarization mode dispersion.

Referring to FIG. 6, a plane polarized mode 110 at angle θ to an arbitrary set of axes 112 is shown propagating down a fiber 114 where it encounters a stressed length of fiber 116 that results in photo-elastic deformation and creation of birefringent axes 118. The plane polarized mode is split into components 120 and 122 on the birefringent axes and after propagating a distance along the stressed part of the fiber these components become separated by a phase 124 due to the different propagation constants in the birefringent axes. This results in the well understood elliptically polarized light 126. This effect is known as polarization mode dispersion.

Figure 7:
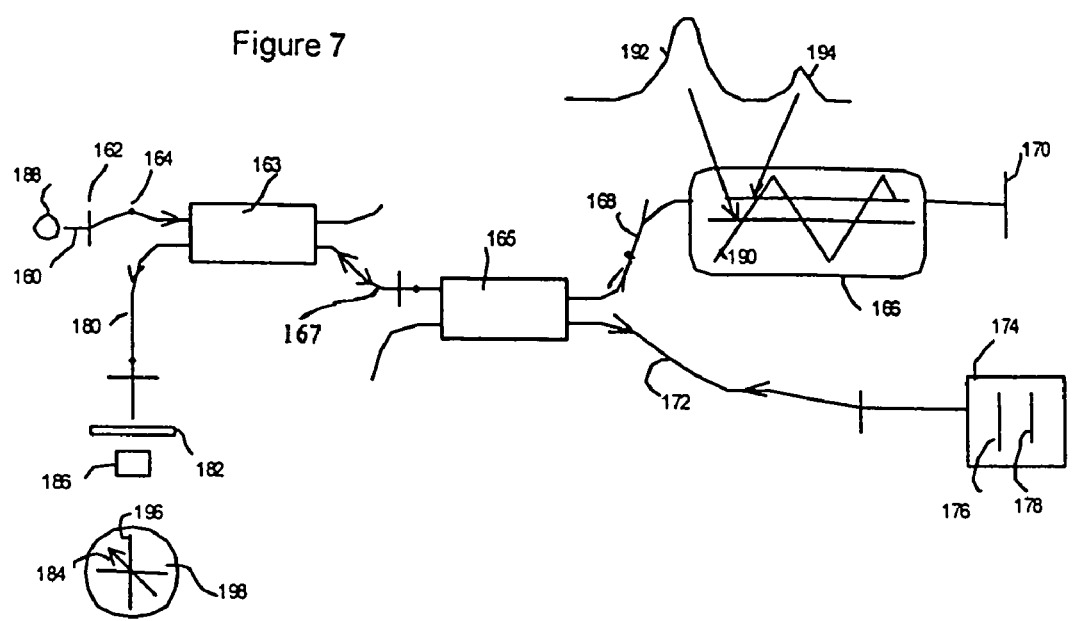
FIG. 7 is a representation of the invention showing a polarization splitter coupler as the beam splitter for a Michelson interferometer and a second PM coupler to allow the signal to be retrieved.

FIG. 7 shows one embodiment of the invention. The broad band light source 188 is input to a fiber optic assembly composed of polarization maintaining fiber 160, having fast and slow birefringent axes supporting fast and slow propagation modes 162 and 164, which are input to a polarization splitter 165. The divided modes follow the reference optical path 168, supporting the p mode 164, shown as a circle, and including an optical path length modulator 166, terminated with a mirror 170. A signal optical path 172 supports the s mode 162, shown as a bar, ending within a target volume 174 having reflecting elements 176 and 178. The p and s modes 162 and 164 from the recombination through the polarization splitter 165 are coupled out of the fiber path 167 by the 3 dB coupler 163 into the output fiber pigtail 180. An analyzer 182 having an axis 184 set at 45 degrees to the p and s fiber axes 196 and 198 respectively allows components of the p and s modes to beat together as a single fringe and can be detected by the detector 186.

The operation of the interferometer is by changing the reference path length in a regular manner using the modulator 166 to scan for targets that would give a burst of fringes within an envelope, when the optical path length of the reference and signal arms pass through the zero optical path difference state. A triangular path change 190 is shown that results in the envelopes 192 and 194 for the target elements 176 and 178. Envelope 192 has a higher intensity as it is nearer the tip of the signal fiber 172.

Polarization mode dispersion and cross coupled components from splicing and any other manufacturing techniques will have the effect of adding other interference signals, spatially coincident but temporally separated. As the signal and reference fiber paths are in p and s modes which have different propagation constants the temporal position of other signals is proportional to the difference in their actual optical path lengths alternating in the p and s modes. The desired signal is separated from the other signals by a selection of the reference fiber mean length and the modulation (fiber stretch) range. Care is exercised in assembly such that splices and components are positioned to minimize zero optical path difference coincidences due to cross coupling.

The path length modulator 166 is implemented by a piezo-electric actuator driving a fiber stretching device; such devices are commercially available with very low polarization mode dispersion.

Sources are typically super luminescent diodes and edge emitting LED's.

It is to be understood and within the spirit and scope of the present invention that any means of splitting the input light which can be in any state of polarization as long as there is some light in both the fast and slow axis (S and P modes) of the fiber, that propagates the S mode into the reference arm and the P mode into the signal arm achieves the desired result.

It is also possible to use a micro-optic coupler with input and output polarization maintaining fibers orientated such that fast and slow axes are orthogonal at one output. The differences between true fiber optic devices and hybrid fiber/micro-optic devices are illustrated in FIGS. 8, 9 and 10.

Figure 8:
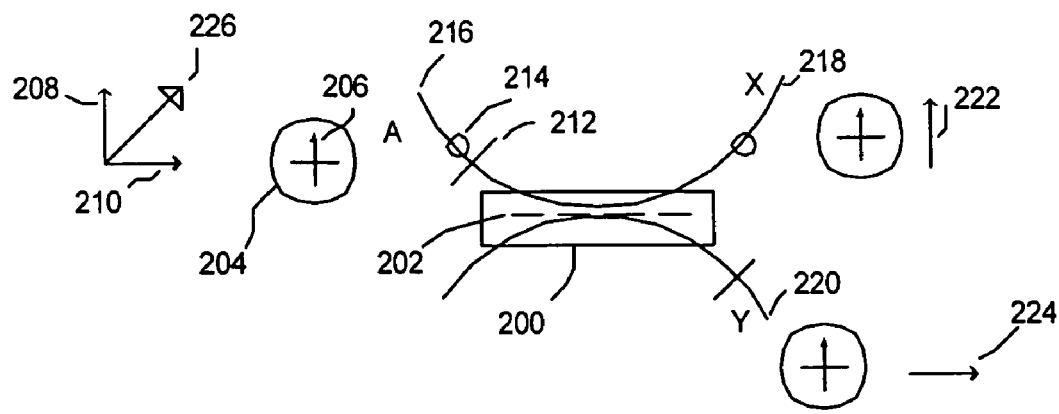
FIG. 8 is a representation of a fiber optic evanescent wave polarization splitter coupler.

Referring to FIG. 8 an all fiber evanescent wave coupler 200 is shown having a polarization splitting film 202. The fiber section 204 is shown as polarization maintaining having a fast, s polarization mode, axis 206 that corresponds longitudinally in the fiber as axis 214. Input plane polarized light 226 is split into fast (s mode) and slow (p mode) components 208 and 210 respectively and input at port 216 (A). Fast component 208 propagates along the fiber axis 214 and is not coupled, being output at port 218 (X) as fast axis component 222. The slow axis "p" polarization mode, component 210, propagates along axis 212 and is fully coupled to the output port 220 (Y) as a slow axis component 224.

Figure 9:
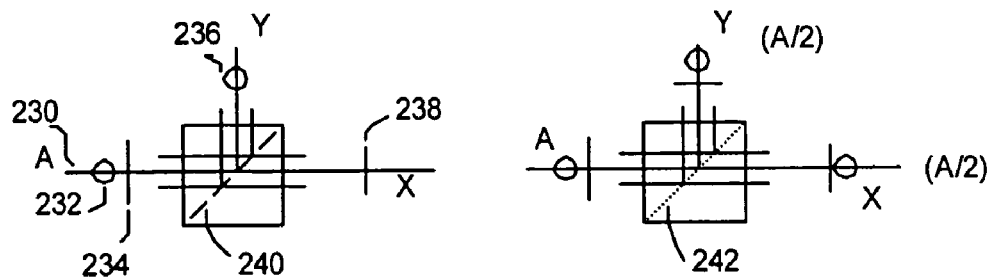
FIG. 9 illustrates polarization and amplitude splitting by bulk optic cube beam splitters.
Figure 10:
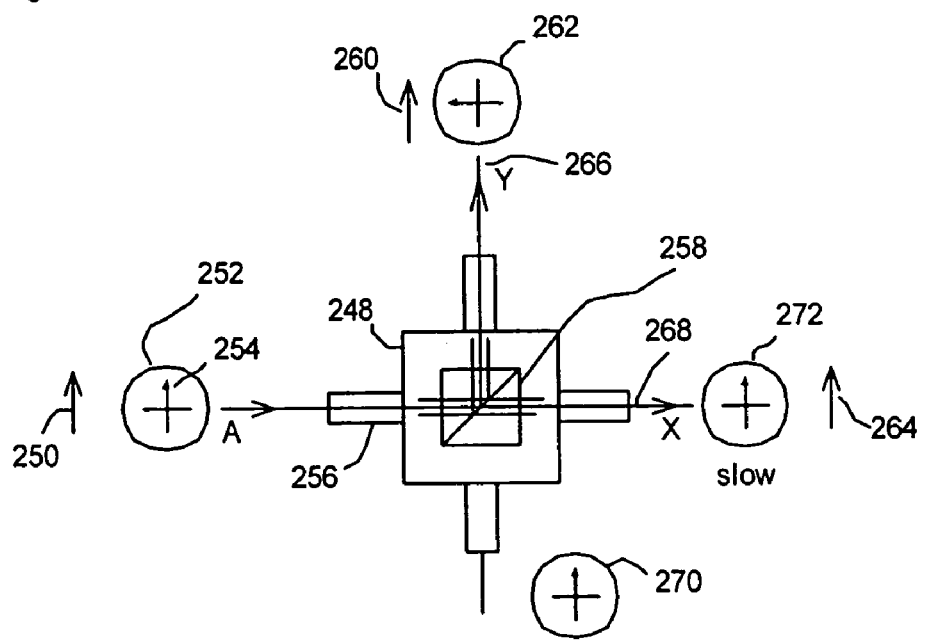
FIG. 10 shows a micro-optic coupler that contains an amplitude beam splitter, and collimating optics for fiber optic inputs/outputs.

Referring to FIG. 9 two beam splitters are shown with polarization splitting film 240 and amplitude splitting film 242. Film 240 corresponds to the film 202 in the coupler of FIG. 8. The s and p modes input at port 230 (A) can be seen to be split and output at port 236 as s mode and at port 238 as P mode. The film 240 is fully reflecting for the s mode and fully transmitting for the p mode. This is analogous to non coupled s mode and fully coupled p mode in an evanescent wave polarization splitter coupler.

The film 242 in the second beam splitter has a 50% reflectance and 50% transmittance, independent of polarization mode. This corresponds to a polarization maintaining evanescent wave coupler with a 50% coupling ratio.

Referring to FIG. 10 a micro-optic coupler 248 contains a micro cube beam splitter 258 and has 4 ports that are fiber collimators illustrated by input port 256. The fibers are orientated as shown in sections 252, 262, 272 and 270 where 262 is rotated 90 degrees with respect to the other three ports. The light 250 input on the fast axis of the fiber 254 is split by the cube 258 and is output at ports 266 and 268.

The fiber at port 266, being rotated 90 degrees has the p and s modes interchanged, independent of the beam splitter 258 polarization sensitivity. If a polarization splitting film is chosen then light must be input at 45 degrees to enable both p and s modes to be illuminated.

Although the invention is described in terms of its preferred embodiment, it is understood that the invention is not so restricted.

The invention claimed is:

1. A scanning interferometer comprising:
   i) a light source;
   ii) a fiber optic assembly comprising:
      a) polarization maintaining fiber having P and S modes;
      b) splitting means for splitting the P and S modes of said fiber wherein said S mode propagates in one arm in one polarization axis and said P mode propagates in the other arm in the other polarization axis;
      c) an optical path length modulator; and
      d) a reference mirror.

2. An interferometer as claimed in claim 1 wherein said polarization maintaining fiber has fast and slow birefringent axes supporting fast and slow propagation modes.

3. An interferometer as claimed in claim 1 further comprising an analyzer.

4. An interferometer as claimed in claim 1 further comprising a detector.

5. An interferometer as claimed in claim 1 wherein said modulator is a piezo-electric actuator and a fiber stretching device.

6. An interferometer as claimed in claim 5 wherein said fiber stretching device has a low polarization mode dispersion.

7. An interferometer as claimed in claim 1 wherein said light source is a super luminescent diode.

8. An interferometer as claimed in claim 1 wherein said light source is an edge emitting light emitting diode.

9. An interferometer as claimed in claim 1 wherein said splitting means is a polarization splitter.

10. A scanning interferometer comprising:
   i) a light source;
   i) a fiber optic assembly comprising:
      a) polarization maintaining fiber having P and S modes;
      b) splitting means for splitting the P and S modes of said fiber wherein said S mode propagates in one arm in one polarization axis and said P mode propagates in the other arm in the other polarization axis;
      c) an optical path length modulator; and
      d) a reference mirrors;
   where said splitting means is a coupler having four polarization maintaining fiber ports, one of which is orientated with birefringent axes orthogonal to the other three ports.

11. A scanning interferometer comprising:
   i) a light source comprising a super luminescent diode or an edge emitting light emitting diode;
   ii) a fiber optic assembly comprising:
      a) polarization maintaining fiber having P and S modes;
      b) splitting means for splitting the P and S modes of said fiber wherein said S mode propagates in one arm in one polarization axis and said P mode propagates in the other arm in the other polarization axis;
      c) an optical length modulator comprising a piezo-electric actuator and a fiber stretching device having a low polarization mode dispersion;
      d) a reference mirror;
      e) an analyzer; and
      f) a detector.

12. A scanning interferometer comprising;
   i) a light source;
   ii) a fiber optic assembly comprising:
      a) polarization maintaining fiber having P and S modes;
      b) splitting means for splitting the P and S modes of said fiber wherein said S mode propagates in one arm in one polarization axis and said P mode propagates in the other arm in the other polarization axis;
      c) an optical path length modulator; and
      d) a reference mirrors;
   where said splitting means is a coupler having four polarization maintaining fiber ports, one or two of which is orientated with birefringent axes orthogonal to the other three ports.

* * * * *